(12) United States Patent
Kindel et al.

(10) Patent No.: US 8,226,931 B2
(45) Date of Patent: Jul. 24, 2012

(54) MIXTURE WITH WINTERGREEN ODOR AND FLAVOR

(75) Inventors: Günter Kindel, Höxter (DE); Gerhard Krammer, Holzminden (DE); Horst Surburg, Holzminden (DE); Hubert Loges, Höxter (DE); Arnold Machinek, Holzminden (DE)

(73) Assignee: Symrise AG, Holzminden (DE)

( * ) Notice: Subject to any disclaimer, the term of this patent is extended or adjusted under 35 U.S.C. 154(b) by 1460 days.

(21) Appl. No.: 10/595,815

(22) PCT Filed: Nov. 12, 2003

(86) PCT No.: PCT/EP03/12648
§ 371 (c)(1),
(2), (4) Date: May 25, 2007

(87) PCT Pub. No.: WO2005/048964
PCT Pub. Date: Jun. 2, 2005

(65) Prior Publication Data
US 2007/0280892 A1    Dec. 6, 2007

(51) Int. Cl.
*A61K 8/00* (2006.01)
(52) U.S. Cl. ......................................................... 424/49
(58) Field of Classification Search .................. 424/49
See application file for complete search history.

(56) References Cited

U.S. PATENT DOCUMENTS 5,628,986 A * 5/1997 Sanker et al. .................. 424/49
5,688,491 A * 11/1997 Shahidi ........................... 424/49
5,795,616 A * 8/1998 Greenberg .................... 426/650

FOREIGN PATENT DOCUMENTS

FR       2398831      5/2003
WO      03/022256    5/2003

OTHER PUBLICATIONS

The Good Scents Company: "Salicylaldehyde" (http://web.archive.org/web/20030719115435/http://www.thegoodscentscompany.com/data/rw1028641.html).*
Heath, Henry B.( Source Book of Flavors. NY: Van Nostrand Reinhold, 1981. ).*
m-dimethoxybenzene (Food and Chemical Toxicology, vol. 38, Supplement 3, 2000, pp. s59-s62.).*
MedicineNet.com (Taste and Smell. http://www.medicinenet.com/script/main/art.asp?articlekey=212; Oct. 24, 2002).*
The Good Scents Company: "Salicylaldehyde" (http://web.archive.org/web/20030719115435/http://www.thegoodscentscompany.com/data/rw1028641. html). Jul. 19, 2003.*

* cited by examiner

*Primary Examiner* — Frederick Krass
*Assistant Examiner* — Chris Simmons
(74) *Attorney, Agent, or Firm* — Roylance, Abrams, Berdo & Goodman, L.L.P.

(57) ABSTRACT

The invention relates to a mixture of compounds having the sensory properties of wintergreen, to fragrance and flavoring compositions containing said mixture and to flavored and perfumed products containing said mixture, to a method of adding a wintergreen flavor, odor or note to (non-wintergreen) flavored or perfumed products. Further the present invention relates to the use of said mixture as an enhancement, or as complete or partial replacement for methyl salicylate, in particular in chewing gum, foods, dentrifices, mouthwashes and other orally consumable products. The mixture comprises or consists of dihydroanethole, o-anisaldehyde, 1,3-dimethoxybenzene, 2'-hydroxyacetophenone, and optionally 2-methoxyacetophenone.

19 Claims, No Drawings

MIXTURE WITH WINTERGREEN ODOR AND FLAVOR

FIELD OF THE INVENTION

The invention relates to a mixture of compounds having the sensory properties of wintergreen, to fragrance and flavoring compositions containing said mixture and to flavored and perfumed products containing said mixture, to a method of adding a wintergreen flavor, odor or note to (non-wintergreen) flavored or perfumed products. Further the present invention relates to the use of said mixture as an enhancement, or as complete or partial replacement for methyl salicylate, in particular in chewing gum, foods, dentrifices, mouthwashes and other orally consumable products.

BACKGROUND OF THE INVENTION

Methyl salicylate (2-hydroxybenzoic acid methyl ester) is a commonly used flavorant. It is the major constituent of wintergreen oil which can be obtained by steam destillation from parts of the plant, typically the leaves. Methyl salicylate is also produced by esterification of salicylic acid with methanol.

The sensory properties (odor and taste) of methyl salicylate are described as warm, sweet, phenolic, wintergreen.

Methyl salicylate is a commonly used flavor and fragrance compound which provides the sensory properties of wintergreen. It is used in perfumes, foods, beverages, candies, chewing gums, oral care products and so forth. It is also used to enhance the flavor of mint flavored products, for example, those flavored primarily with peppermint or spearmint oils.

Methyl salicylate is also used as an active ingredient in topically applied anesthetic ointments promoted for relief of muscle aches, arthritis and similar complaints. Salicylic acid derivatives, most notably acetyl salicylic acid (more commonly known as aspirin), often have pharmaceutical properties such as anagestic, anticoagulant, antipyretic and antifungal activity. Not surprisingly, these pharmaceutical agents are generally toxic to some degree. Methyl salicylate itself is known to be toxic above certain dosage levels.

While products flavored with methyl salicylate have gained widespread consumer acceptance, the use of such a compound with pharmaceutical properties and a degree of toxicity poses a potential risk of adverse publicity or governmental regulation which could limit the level at which it may be used, or prohibit it entirely.

Furthermore methyl salicylate is not stable in alkaline media. This instability in alkaline media limits the number and type of compositions and products into which methyl salicylate may successfully be incorporated.

The availability of a replacement compound for methyl salicylate would be highly desirable.

U.S. Pat. No. 5,795,616 relates to the use of 2'-hydroxypropiophenone as a flavor ingredient. More particularly it relates to the use of 2'-hydroxypropiophenone as an enhancer, or as complete or partial replacer for methyl salicylate in chewing gum, foods, dentrifices, mouthwashes and other orally consumable compositions. Although this document describes the use of 2'-hydroxypropiophenone as a flavor and as a replacer for methyl salicylate, the best results are obtained when using a mixture of 2'-hydroxypropiophenone and methyl salicylate. The preferred replacement level of methyl salicylate is about 10 to 50% by weight.

WO 01/68044 describes oral compositions comprising a wintergreen flavor imparting ingredient and having an alkaline pH, wherein the wintergreen flavor imparting ingredient is 2'-hydroxypropiophenone.

Until now, it is believed that no satisfactory, non-salicylate substitute for methyl salicylate in fragrance and/or flavoring compositions has been proposed.

SUMMARY OF THE INVENTION

The present invention provides for a mixture MS having the sensory properties of wintergreen. Mixture MS comprises or consists of compounds A, B, C and D:

Mixture MS:

| | Compound | Synonyms | CAS-# | FEMA-# |
|---|---|---|---|---|
| A | 1-methoxy-4-propyl-benzene | dihydroanethole; p-propylanisole | 104-45-0 | 2930 |
| B | 2-methoxy-benzaldehyde | o-anisaldehyde | 135-02-4 | — |
| C | 1,3-dimethoxy-benzene | resorcinol dimethyl ether; m-methoxyanisole | 151-10-0 | 2385 |
| D | 1-(2-hydroxyphenyl)-ethanone | 2'-hydroxy-acetophenone; o-acetylphenole | 118-93-4 | 3548 |

Optionally, the mixture MS is rounded off by adding an amount of compound E:

| | Compound | Synonyms | CAS-# | FEMA-# |
|---|---|---|---|---|
| E | 1-(2-methoxyphenyl)-ethanone | 2'-methoxy-acetophenone; acetylanisole | 579-74-8 | — |

It is a feature and one main advantage of the present invention to provide a wintergreen flavor, odor or note to fragrance and flavoring compositions and perfumed or flavored products with the mixture MS according to the present invention, preferably without the use of methyl salicylate and/or ethyl salicylate.

Fragrance or flavoring compositions according to the present invention comprise an organoleptically effective amount of mixture MS. Preferably, such fragrance or flavoring compositions possess a wintergreen flavor or odor (i) resulting from or (ii) enhanced by the amount of the mixture present.

The present invention further provides improved perfumed or flavored products. In the present invention, the term "flavored products" refers to manufactured goods which are intended to be orally consumed or at least taken into the oral cavity.

The present invention provides for the use of mixture MS in fragrance and flavoring compositions used in perfumed or flavored products to enhance or replace methyl salicylate. When used as a replacement for methyl salicylate, the replacement may be partial or complete.

In accordance with one embodiment of the present invention a wintergreen-flavored product comprising, as a flavorant or odorant, methyl salicylate is enhanced by addition of mixture MS. Preferably, the weight ratio of methyl salicylate to mixture MS in the perfumed or flavored product is between about 10:1 and 1:20, more preferably between about 4:1 and 1:10.

In an embodiment of the invention the pH of the fragrance or flavoring composition or perfumed or flavored product is alkaline. By this is meant that the pH ranges from about 7.5 to about 12. In a particular embodiment the pH is greater than 7.5, preferably the pH is between about 8.5 and 10.5.

In an embodiment, a method of reducing the level of methyl salicylate in a wintergreen fragrance and flavoring composition is provided. The method comprises the steps of modifying a wintergreen-flavored product formulation by substituting mixture MS for at least a portion of the methyl salicylate. In a preferred embodiment, all of the methyl salicylate is replaced.

Further aspects of the present invention are defined in the attached claims and will become apparent from the further description.

DETAILED DESCRIPTION OF THE INVENTION

The present invention provides a non-salicylate mixture, hereinafter also "mixture MS", which has a very similar sensory profile to methyl salicylate and which can replace methyl salicylate. This allows mixture MS to be substituted for methyl salicylate at any level of the original quantity of methyl salicylate, depending on the application.

Mixture MS comprises or consists of compounds A, B, C and D, and optionally compound E. It is believed that mixture MS as such is new.

Preferably, in mixture MS the amounts of compounds A), B) C), and D) and the ratio of compounds A):B):C):D) are adjusted so that the mixture provides a wintergreen flavor or odor.

Preferred amounts by weight of these compounds in the inventive mixture MS are:

| | Compound | Synonyms | parts by weight |
|---|---|---|---|
| A | 1-methoxy-4-propyl-benzene | dihydroanethole | 5-80 |
| B | 2-methoxybenzaldehyde | o-anisaldehyde | 10-90 |
| C | 1,3-dimethoxybenzene | m-methoxyanisole | 100-500 |
| D | 1-(2-hydroxyphenyl)-ethanone | 2'-hydroxy-acetophenone | 100-500 |
| E | 1-(2-methoxyphenyl)-ethanone | 2'-methoxy-acetophenone | 0-200 |

Preferably, the weight ratios the compounds A:B:C:D:E in mixture MS are or are about 5-80:10-90:100-500:100-500:0-200, more preferably about 10-40:20-70:150-400:150-400:50-150.

The sensory properties of the individual compounds A to E are as follows (Leffingwell & Associates—Database, Flavor-Base Professional 2001, Tobacco Edition, GRAS & EC Flavor Chemicals Report):

| | Compound | Sensory description |
|---|---|---|
| A | 1-methoxy-4-propyl-benzene | Sweet, herbaceous, anise-like odor and taste |
| B | 2-methoxybenzaldehyde | Sweet spicy, floral, anisic, cinnamate-like aroma, spicy taste |
| C | 1,3-dimethoxybenzene | Sweet, floral, earthy, root-beer, chemical, medicinal, spice, cooling |
| D | 1-(2-hydroxyphenyl)-ethanone | Sharp, cherry-almond-hawthorne-hay, cinnamon, naphthyl, cherry pit, coumarin, phenolic, tobacco, honey |

-continued

| | Compound | Sensory description |
|---|---|---|
| E | 1-(2-methoxyphenyl)-ethanone | Herbaceous, phenolic, wintergreen, chemical, medicinal, dusty |

Since none of the compounds A to D exhibits wintergreen odor or flavor it is thus very surprising that mixing compounds A to D yields a mixture that has the typical wintergreen flavor and odor.

The sensory properties of the mixture MS according to the invention and methyl salicylate respectively were assessed at equal concentrations in a sweet water taste test. 500 mg of the mixture MS according to the invention and methyl salicylate were dissolved separately in 10 mL of ethanol. 1 mL of this solution was dissolved in 100 mL of a 5% wt. sugar aqueous solution.

The weight ratios the compounds A:B:C:D in mixture MS here were 20:40:250:250.

The sensory properties were assessed according to the following descriptors, each on a scale of 1 (very weak) to 10 (very strong).

| Descriptor | Methyl salicylate | Mixture MS |
|---|---|---|
| Wintergreen | 8 | 7 |
| Sweet | 7 | 7 |
| Medicinal | 7 | 6 |
| Phenolic | 5 | 5 |
| Impact | 7 | 8 |
| Strength | 8 | 8 |

When compound E is added to a mixture consisting of compounds A to D, the sensory properties of the mixture become even more balanced and even closer to methyl salicylate.

When o-anisaldehyde is replaced by the same amount of p-anisaldehyde, the sensory properties of such a mixture can be described as more coumarinic, vanillic, green woodruff which is not typical for wintergreen.

As mentioned before, the fragrance or flavoring compositions according to the present invention preferably possess a wintergreen flavor or odor (i) resulting from or (ii) enhanced by the amount of the mixture present. In some preferred embodiments, the fragrance or flavoring compositions according to the present invention comprise methyl salicylate. In those cases the ratio in parts by weight of methyl salicylate:mixture MS (mixture of A), B), C), and D)) is typically in the range of from 10:1 to 1:20, preferably in the range of from 4:1 to 1:10.

Perfumed or flavored products according to the present invention favorably comprise (i) mixture MS or (ii) a fragrance or flavoring composition according to the present invention (the composition itself comprising mixture MS).

Preferably, the product possesses a wintergreen flavor or odor (i) resulting from or (ii) enhanced by the amount of mixture MS present.

In preferred embodiments, the perfumed or flavoured product according to the present invention is a chewing gum, a toothpaste or a mouthwash.

Preferred products according to the present invention have a pH from about 7.5 to about 12, in particular if they do not comprise any methyl salicylate.

Favourably, a perfumed product according to the present invention contains about 0.05 to 5% by weight of mixture MS (mixture according to the present invention). A flavored product according to the present invention contains preferably about 0.05 to 2% by weight of mixture MS.

Depending on the individual demands, a product according to the present invention comprises methyl salicylate or not. In preferred embodiments, the product comprises (i) no or (ii) less than an organoleptically effective amount or (iii) less than 0.1% by weight of methyl salicylate. These products very often are adjusted to a pH of from 7.5 to 12 (see above).

The present invention also provides for a method of (either) adding a wintergreen odor, flavor or note to a product or enhancing the wintergreen odor, flavor or note of a product. The method comprises the step of adding to the product or incorporating into the product an effective amount of (a) mixture MS (mixture according to the present invention) or (b) a fragrance or flavoring composition according to the present invention. Favorably, the product after addition of (a) mixture MS or (b) the composition according to the present invention comprises (i) no or (ii) less than an organoleptically effective amount or (iii) less than 0.1% by weight of methyl salicylate. Again, the product is favorably a chewing gum, a toothpaste or a mouthwash.

The present invention further provides a method of reducing the level of methyl salicylate in a wintergreen fragrance or flavoring composition, the method comprising the step of substituting a portion or all of the methyl salicylate in the composition by mixture MS (i.e. a mixture according to the present invention).

Ingredients which may be present in the perfumed and flavored products according to the invention can have additional effects. Examples which may be mentioned are: preservatives, abrasives, anti-acne agents, agents against skin ageing, antibacterial agents, anticellulite agents, antidandruff agents, anti-inflammatory agents, irritation-preventing agents, irritation-suppressing agents, antimicrobial agents, antioxidants, astringents, perspiration-suppressing agents, antiseptics, antistatics, binders, buffers, carrier materials, chelating agents, cell stimulants, cleansing agents, care agents, hair-removal agents, surface-active substances, deodorizing agents, antiperspirants, softeners, emulsifiers, enzymes, essential oils, fibres, film formers, fixatives, foam formers, foam stabilizers, antifoams, foam boosters, fungicides, gelling agents, gel-forming agents, haircare agents, hair-shaping agents, hair-smoothing agents, moisture-donating agents, moisturizing substances, humectant substances, bleaching agents, strengthening agents, stain-removal agents, optical brighteners, impregnating agents, soil repellants, friction-reducing agents, lubricants, moisturizing creams, ointments, opacifiers, plasticizing agents, covering agents, polish, sheen agents, polymers, powders, proteins, refatting agents, abrasive agents, silicones, skin-calming agents, skin-cleansing agents, skin care agents, skin-healing agents, skin-lightening agents, skin-protecting agents, skin-softening agents, cooling agents, skin-cooling agents, warming agents, skin-warming agents, stabilizers, UV-absorbing agents, UV filters, washing agents, softeners, suspending agents, skin-tanning agents, thickeners, vitamins, oils, waxes, fats, phospholipids, saturated fatty acids, mono- or polyunsaturated fatty acids, -hydroxy acids, polyhydroxy fatty acids, liquefying agents, dyes, colour-protection agents, pigments, anti-corrosives, aromas, flavours, fragrances or other customary constituents of a cosmetic or dermatological formulation, such as alcohols, polyols, electrolytes, organic solvents or silicone derivatives.

Also advantageous is the combination of cooling agents with mixture MS. Examples of cooling agents which may be mentioned are: 1-menthol, menthoneglycerol acetal, menthyl lactate, substituted menthyl-3-carboxamides (e.g. N-ethyl-menthyl-3-carboxamide), 2-isopropyl-N,2,3-trimethylbutanamide, substituted cyclohexanecarboxamides, 3-menthoxypropane-1,2-diol, 2-hydroxyethyl menthylcarbonate, 2-hydroxypropyl menthylcarbonate, N-acetylglycine menthyl ester, menthyl hydroxycarboxylates (e.g. menthyl-3-hydroxybutyrate), monomenthyl succinate, 2-mercaptocyclodecanone, menthyl-2-pyrrolidin-5-onecarboxylate.

In new flavor formulations and flavoring compositions, mixture MS may be used as the sole flavorant or it may be combined with other flavor compounds to impart a wintergreen flavor or wintergreen note to the composition. More particularly, the mixture MS according to the present invention may be advantageously blended with peppermint oil, spearmint oil, menthol, cinnamon flavor, anise, root beer flavor, bubble gum flavor, spice flavors, citrus oils and fruit flavors. Such flavoring compositions may include natural or artificial components or blends of the two. Combinations of the mixture MS according to the present invention with cooling agents such as menthol, menthone ketals, N-substituted-p-menthane carboxamides and 3-1-menthoxypropane-1,2-diol are specifically completed.

The mixture MS according to the present invention produces surprising enhancing effects in fragrance compositions and perfumed products as well as an individual fragrance as together with other fragrances.

As mentioned, the fragrance or flavoring composition according to the present invention comprises an organoleptically effective amount of mixture MS.

In the fragrance compositions according to the present invention, the amount of the mixture MS according to the present invention used is generally about 0.05 to 99% by weight, preferably 5 to 90% by weight, and more preferably 10 to 70% by weight based on the total fragrance composition.

In the flavoring compositions according to the present invention, the amount of mixture MS according to the present invention used is generally about 0.05 to 99% by weight, preferably 1 to 80% by weight, and more preferably 5 to 50% by weight based on the total flavoring composition.

In general flavored products according to the present invention will contain a flavoring composition according to the present invention in about 0.05 to 5%, typically about 0.2 to 2% by weight of final flavored product.

In general the perfumed product according to the present invention will contain a fragrance composition according to the present invention in about 0.05 to 5%, typically about 0.2 to 2% by weight of final perfumed product.

Typically the perfumed product will contain mixture MS according to the present invention in about 0.05 to 5%, preferably in about 0.1 to 2% by weight of final perfumed product.

Typically the flavored product will contain the mixture MS according to the present invention in about 0.05 to 2%, preferably in about 0.1 to 0.5% by weight of final flavored product.

The precise usage level will depend on the nature of the desired fragrance or flavoring composition of the final product and the preferences of the perfumer or flavorist compounding the flavor composition.

Flavored products include foods, beverages, confections, pharmaceuticals, chewing gums, mouthwashes, toothpastes and other items meeting the above definition. The flavored products, in particular oral compositions, may be in any form common in the art, e.g. paste, gel, mousse, aerosol, gum, lozenge, powder, cream etc. and may also be formulated into systems for use in dual-compartment dispensers.

The present invention in particular contemplates the use of mixture MS as a flavorant for oral care products and confectionery products, for example chewing gums, candies, edible films, breath freshening capsules, pharmaceutical preparations, dentrifices, toothpastes, mouth washes and the like. In products where methyl salicylate is presently used, mixture MS may be used to enhance the wintergreen flavor or to replace a portion or all of that compound.

In a preferred embodiment, the flavored product is a chewing gum. Such chewing gums typically contain about 0.25 to about 3%, and most typically about 0.8 to 1.5% of total flavor by weight.

In general, such chewing gum comprises a water-soluble bulk portion, a water-insoluble chewable gum base portion and typically, water-insoluble flavor ingredients.

The water-soluble bulk portion dissipates with a portion of the flavor over time during chewing. The gum base portion is retained in the mouth throughout the chew.

The insoluble gum base generally comprises elastomers, resins, fats and oils, waxes, softeners and inorganic fillers. The insoluble gum base constitutes between about 5% to about 95% of the gum, and more preferably about 20% to 30%. All percent values represent weight percent.

The gum base typically also includes a filler component. The filler component may be calcium carbonate, magnesium carbonate, talc, dicalcium phosphate, and the like. The filler may constitute between about 5% to about 60% of the gum base. Preferably, the filler comprises about 5% to about 50% of the gum base. The gum base also contains softeners, including glycerol monostearate and glycerol triacetate. Further, gum bases may also contain additional ingredients such as antioxidants, colors, and emulsifiers. The present invention contemplates using any commercially acceptable gum base.

The water-soluble portion of the chewing gum may further comprise softeners, sweeteners, and flavors and combinations thereof. The softeners are added to the chewing gum to optimize the chewing ability and mouth feel of the gum. Softeners, also known in the art as plasticizers, generally constitute about 0.1% to about 15% of the chewing gum. Softeners contemplated by the present invention include glycerin, lecithin and combinations thereof. Aqueous sweetener solutions such as those containing sorbitol, hydrogenated starch hydrolysates, corn syrup, and combinations thereof may be used as softeners and binding agents in gum.

Sweeteners contemplated by the present invention for use in the chewing gum include both sugar and sugarless components. Sugar sweeteners generally include saccharide-containing components commonly known in the art and include, but are not limited to, sucrose, dextrose, maltose, dextrin, dried invert sugar, fructose, levulose, galactose, corn syrup solids and the like, alone or in any combination. Sugarless sweeteners include components with sweetening characteristics but are devoid of the commonly known sugars and comprise, but are not limited to, sugar alcohols such as sorbitol, mannitol, xylitol, hydrogenated starch hydrolysates, maltitol, hydrogenated isomaltulose, Tagatose® and the like, alone or in any combination. Also contemplated for direct addition to the gum are high intensity sweeteners such as aspartame, sucralose, cyclamate, acesulfame-K, dihydrochalones, glycyrrhizin, alitame, and saccharin, and the food acceptable salts thereof.

Those persons skilled in the art will recognize that any combination of sugar/sugarless sweeteners may be employed in the chewing gum. Further, those skilled in the art will recognize a sweetener may be present in a chewing gum in whole or in part as a water-soluble bulking agent, and that the softener may be combined with a sweetener such as an aqueous sweetener solution.

In general, the chewing gum is manufactured by sequentially adding the various chewing gum ingredients to any commercially available mixer known in the art. After the ingredients have been thoroughly mixed, the gum mass is discharged from the mixer and shaped into the desired forms such as by rolling into sheets and cutting into sticks, extruding into chunks, or casting into pellets. Generally, the ingredients are mixed by first melting gum base and adding it to the running mixer. The base may also be melted in the mixer itself. Color may also be added at this time. A softener such as glycerin may then be added next along with the syrup and a portion of bulking agent. Further portions of the bulking agents may be added to the mixer.

Preferably, the flavor ingredients are added to the gum mixture near the end of the mixing process. The entire mixing procedure takes from about 5 minutes to 15 minutes, however, longer mixing times may be required. Those persons skilled in the art will recognize that many variations of the above described procedure may be followed.

In a preferred embodiment, the flavored product is a toothpaste.

Toothpastes that are flavored with the inventive mixture MS generally consist of an abrasive system (abrasives or polishes), for example silicic acids, calcium carbonates, calcium phosphates, aluminum oxides and/or hydroxyl apatites; surface-active substances, for example sodium lauryl sulphate, sodium lauryl sarcosinate and/or cocamidopropylbetaine; humectants, for example glycerol and/or sorbitol; thickeners, for example carboxymethyl cellulose, polyethylene glycols, carrageenans and/or Laponites®, sweeteners, for example saccharin; stabilizers; and active compounds, for example sodium fluoride, sodium monofluorophosphate, tin difluoride, quaternary ammonium fluorides, zinc citrate, zinc sulphate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide and/or sodium bicarbonate.

In the toothpastes and chewing gum, the inventive mixture MS generally is used at a concentration between 0.05 and 2% by weight, preferably 0.1 to 1% by weight, and more preferably between 0.1 and 0.5% by weight. In sweets for sucking, the content of the inventive mixture MS is between 0.01 and 2% by weight, preferably 0.05 to 1% by weight; and more preferably between 0.1 and 0.5%.

In another preferred embodiment, the flavored product is a mouth wash.

The content of the inventive mixture MS is, in ready-to-use mouthwashes 0.01 to 1% by weight, preferably 0.1 to 0.5% by weight. In mouthwash concentrates, the content of the compositions comprising the inventive mixture MS according to the present invention is between 0.01 and 20% by weight, preferably 0.1 to 10% by weight, and more preferably 3 to 5% by weight.

It should be addressed that high concentrations, e.g. 5% by weight, in ready-to-use flavored products, result in a less typical wintergreen taste profile, i.e. the phenolic and medicinal notes become stronger than usually accepted and liked by the consumer.

When finished products that comprise the inventive mixture MS are used, it is found that the inventive mixture MS or the compositions comprising the inventive mixture MS are particularly suitable for freshening the breath and neutralizing or reducing bad breath.

The use of the inventive mixture MS or the compositions comprising said mixture in oral care products, for example mouthwashes and toothpastes, and chewing-gum, leads to unpleasant, especially bitter, taste impressions being masked or neutralized, as are caused, for example, by substances such as triclosan, zinc citrate, zinc sulphate, polyphosphates and pyrophosphates, bicarbonates, strontium salts and potassium salts, tin pyrophosphate, tin chloride, aluminum lactate, hydrogen peroxide, fluorides, vitamins, cetylpyridinium chloride, and emulsifiers, for example, particularly sodium lauryl sulphate, sodium lauryl sarcosinate and cocamidopropylbetaine, and sweeteners, for example aspartame, saccharin, acesulfame-K, sorbitol; xylitol, cyclamates (for example sodium cyclamate), sucralose, alitame, neotame, thaumatin, neohesperidin DC, maltitol, lactitol or chewing-gum bases.

A further positive property of the inventive mixture MS to be emphasized is their stability in toothpastes based on chalk or bicarbonate into which, due to their alkaline pH, a flavoring is difficult to be incorporated.

Examples of aromas, flavors and fragrances for use in products according to the present invention can be found, for example, in K. Bauer, D. Garbe and H. Surburg, Common Fragrance and Flavor Materials, 4$^{th}$. Ed., Wiley-VCH, Weinheim 2001.

Specifically, mention may be made of:

extracts from natural raw materials such as essential oils, concretes, absolutes, resins, resinoids, balsams, tinctures, such as, for example, ambergris tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill herb oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orangeflower absolute; orange oil; origanum oil; palmarosa oil; patchouli oil; perilla oil; Peruvian balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmation sage oil; Spanish sage oil; sandalwood oil; celery seed oil; spike lavender oil; Japanese anise oil; styrax oil; tagetes oil; fir needle oil; tea-tree oil; turpentine oil; thyme oil; Tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil; and fractions thereof, or ingredients isolated therefrom;

individual fragrances from the group of hydrocarbons, such as, for example, 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene;

of aliphatic alcohols, such as, for example, hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-01; (E,Z)-2,6-nonadienol; 3,7-dimethyl-7-methoxyoctan-2-ol; 9-decenol; 10-undecenol; 4-methyl-3-decen-5-ol; of aliphatic aldehydes and 1,4-dioxacycloalken-2-ones thereof, such as, for example, hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde;

of aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; of aliphatic sulfur-containing compounds, such as, for example, 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of aliphatic nitriles, such as, for example, 2-nonenenitrile; 2-tridecenenitrile; 2,12-tridecenenitrile; 3,7-dimethyl-2,6-octadienenitrile; 3,7-dimethyl-6-octenenitrile;

of aliphatic carboxylic acids and esters thereof, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl(E,Z)-2,4-decadienoate; methyl 2-octynoate; methyl 2-nonynoate; allyl 2-isoamyloxyacetate; methyl 3,7-dimethyl-2,6-octadienoate;

of acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof;

of acyclic terpene aldehydes and ketones, such as, for example, geranial; neral; citronellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

of cyclic terpene alcohols, such as, for example, menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates, 3-methyl-2-butenoates thereof;

of cyclic terpene aldehydes and ketones, such as, for example, menthone; isomenthone; 8-mercaptomenthan-3-one; carvone; camphor; fenchone; alpha-ionone; beta-ionone; alphan-methylionone; beta-n-methylionone; alpha-isomethylionone; beta-isomethylionone; alphairone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedarwood oil (methyl cedryl ketone);

of cyclic alcohols, such as, for example, 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols, such as, for example, alpha-3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-01; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers, such as, for example, cineol; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic ketones, such as, for example, 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

of cycloaliphatic aldehydes, such as, for example, 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl 2,4-dimethyl-3-cyclohexen-1-yl ketone;

of esters of cyclic alcohols, such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

of esters of cycloaliphatic carboxylic acids, such as, for example, allyl 3-cyclohexylpropionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolan-2-acetate;

of aromatic hydrocarbons, such as, for example, styrene and diphenylmethane;

of araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

of esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; of araliphatic ethers, such as, for example, 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

of aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

of aromatic and araliphatic ketones, such as, for example, acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

of nitrogen-containing aromatic compounds, such as, for example, 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenenitrile; 5-phenyl-3- methylpentanenitrile; methyl anthranilate; methyl N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; skatole; 2-methoxy-3-isopropyl pyrazine; 2-isobutyl-3-methoxypyrazine;

of phenols, phenyl ethers and phenyl esters, such as, for example, estragole; anethole; eugenole; eugenyl methyl ether; isoeugenole; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

of heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

The fragrance or flavoring compositions comprising mixture MS according to the present invention can be used in liquid form, neat or diluted with a solvent. Suitable solvents for this purpose are, for example, ethanol, isopropanol, diethylene glycol monoethyl ether, glycerol, propylene glycol, 1,2-butylene glycol, dipropylene glycol, diethyl phthalate, triethyl citrate, isopropyl myristate, triacetin etc.

In addition, the fragrance or flavoring compositions comprising mixture MS according to the present invention can be adsorbed on a carrier which serves both to distribute the fragrances or flavors finely within the product and to release them in a controlled manner during use. Such carriers can be porous inorganic materials such as light sulphate, silica gels, zeolites, gypsums, clays, clay granules, gas concrete etc. or organic materials such as woods and cellulose-based substances.

The fragrance or flavoring compositions comprising mixture MS according to the present invention can also be microencapsulated, spray dried, in the form of inclusion complexes or in the form of extrusion products and be added in this form to the perfumed or flavored.

The properties of the fragrance or flavoring compositions modified in this way can optionally be further optimized by "coating" with suitable materials with regard to a more targeted fragrance or flavor release, for which purpose preference is given to using wax-like polymers, such as, for example, polyvinyl alcohol.

The microencapsulation of the fragrance or flavoring compositions can, for example, be carried out by the "coacervation method" using capsule materials made from, for example, polyurethane-like substances or soft gelatin. The spray-dried fragrance or flavoring compositions can, for example, be prepared by spray drying an emulsion or dispersion comprising the fragrance or flavoring compositions, where the carriers used can be modified starches, proteins, dextrin and vegetable gums. Inclusion complexes can be prepared, for example, by introducing dispersions of the fragrance or flavoring compositions and cyclodextrins or urea derivatives into a suitable solvent, e.g. water. Extrusion products can be obtained by melting the fragrance or flavoring compositions with a suitable wax-like substance and by extrusion with subsequent solidification, optionally in a suitable solvent, e.g. isopropanol.

The fragrance compositions comprising mixture MS according to the present invention can be used in concentrated form, in solutions or in the above-described modified form for the preparation of, for example, perfume extracts, eaux de partum, eaux de toilettes, aftershaves, eaux de colognes, pre-shave products, splash colognes and perfumed freshening wipes, and the perfuming of acidic, alkaline and neutral cleaners, such as, for example, floor cleaners, window cleaners, dishwashing detergents, bath and sanitary cleaners, scouring milk, solid and liquid WC cleaners, pulverulent and foam carpet cleaners, liquid laundry detergents, pulverulent laundry detergents, laundry pretreatment agents, such as bleaches, soaking agents and stain removers, fabric softeners, washing soaps, washing tablets, disinfectants, surface disinfectants, and of air fresheners in liquid or gel form or deposited on a solid carrier, aerosol sprays, waxes and polishes, such as furniture polishes, floor waxes, shoe creams, and bodycare compositions, such as, for example, solid and liquid soaps, shower gels, shampoos, shaving soaps, shaving foams, bath oils, cosmetic emulsions of the oil-in-water, water-in-oil and water-in-oil-in-water type, such as, for example, skin creams and lotions, face creams and lotions, sunscreen creams and lotions, aftersun creams and lotions, hand creams and lotions, foot creams and lotions, depilatory creams and lotions, aftershave creams and lotions, tanning creams and lotions, haircare products, such as, for example, hairsprays, hair gels, hairsetting lotions, hair rinses, permanent and semi-permanent hair colorants, hair-shaping compositions, such as cold waves and hair-smoothing compositions, hair tonics, hair creams and lotions, deodorants and antiperspirants, such as, for example, underarm sprays, roll-ons, deodorant sticks, deodorant creams, products in decorative cosmetics, such as, for example, eyeshadows, nail varnishes, foundations, lipsticks, mascara, and of candles, lamp oils, joss-sticks, insecticides, repellents, propellants.

EXAMPLES

The examples below are intended to illustrate the use of the inventive mixture MS (mixture comprising compounds A), B), C), D) and, optionally, E)). However, the use of the inventive mixture MS is not restricted to the examples cited.

Unless indicated otherwise the amounts given are by weight.

Example 1

| Compound | Parts by weight Composition X | Parts by weight Composition Y | Parts by weight Composition Z |
|---|---|---|---|
| Eucalyptol | 100 | 100 | 100 |
| L-Menthol | 500 | 500 | 500 |
| L-Menthyl acetate | 130 | 130 | 130 |
| L-Carvone | 20 | 20 | 20 |
| Anethole | 100 | 100 | 100 |
| Methyl salicylate | 150 | — | 25 |
| Mixture MSa | — | 150 | 125 |

Mixture MSa consisted of 3.7% dihydroanethole, 7.1% of o-anisaldehyde, 44.6% of 1,3-dimethoxybenzene and 44.6% of 2'-hydroxyacetophenone. The percentages are by weight.

Compositions X to Z were mixed and incorporated separately into a silica-based toothpaste. The dosage was 1.2%, based on the total weight of the toothpaste.

Compositions X to Z were mixed and incorporated separately into a chewing gum. The dosage was 1.2%, based on the total weight of the chewing gum.

The sensory properties of the compositions X to Z as such and as flavored products were evaluated by a panel of eight (8) experienced judges. The compositions X to Z and the flavored products showed a typical wintergreen taste, only very slightly differing in some aspects.

Example 2

A transparent tooth gel with capsules having the following formulation was produced, into which mixture MS1 was incorporated.

| Ingredients | Parts by weight |
| --- | --- |
| 1. Sorbitol, 70% strength | 61.50 |
| 2. Distilled water | 11.40 |
| 3. Saccharin | 0.20 |
| 4. Sodium monofluorophosphate | 1.10 |
| 5. Trisodium phosphate | 0.10 |
| 6. Polyethylene glycol PEG 1500 (PEG 32) | 5.50 |
| 7. Abrasive silica gel | 8.00 |
| 8. Thickening silica gel | 8.00 |
| 9. Sodium carboxymethyl cellulose | 0.60 |
| 10. Sodium lauryl sulphate | 1.50 |
| 11. Mixture MS1 | 1.00 |
| 12. Blue and red colored capsules | 1.00 |
| 13. 4-Hydroxybenzoic acid methylester | 0.10 |

Mixture MS1 consisted of 4.5% dihydroanethole, 8.9% of o-anisaldehyde, 37.3% of 1,3-dimethoxybenzene, 34.3% of 2'-hydroxyacetophenone and 15% of 2'-methoxyacetophenone. The percentages are by weight.

The toothpaste had the typical wintergreen flavor.

Example 3

A calcium carbonate based toothpaste (pH=9.6) having the following formulation was produced, into which mixture MS2 was incorporated.

| Ingredients | Parts by weight |
| --- | --- |
| 1. Calcium carbonate | 40.00 |
| 2. Sorbitol | 27.00 |
| 3. Hydrated silica | 2.00 |
| 4. Sodium monofluorophosphate | 0.80 |
| 5. Trisodium phosphate | 0.50 |
| 6. Titanium dioxide | 1.00 |
| 7. Sodium carboxymethyl cellulose | 0.90 |
| 8. Sodium lauryl sulphate | 2.00 |
| 9. Sodium saccharin | 0.20 |
| 10. Sodium fluoride | 0.20 |
| 10. Mixture MS2 | 0.70 |
| 11. Additional flavoring | 0.40 |
| 12. Water | 24.30 |

Mixture MS2 consisted of 2.8% dihydroanethole, 7.0% of o-anisaldehyde, 39.4% of 1,3-dimethoxybenzene, 42.3% of 2'-hydroxyacetophenone and 8.5% of 2'-methoxyacetophenone. The percentages are by weight.

The additional flavoring comprised I-menthol, I-carvone, anethole and the cooling compounds N-ethyl-p-menthane-3-carboxamide, I-menthyllactate, I-menthol glycol carbonate and I-menthol propyleneglycol carbonate.

The flavor and the sensory profile of this alkaline calcium carbonate based toothpaste was stable over a prolonged period of time.

This cooling, long-lasting, breath-freshening toothpaste had a pleasant wintergreen flavor without bitterness or medicinal taste.

Example 4

A ready-to-use mouthwash composition having the following formulation was produced, into which mixture MS2 was incorporated.

| Ingredients | Parts by weight |
| --- | --- |
| Ethanol | 7.00 |
| Glycerin | 12.00 |
| Sodium fluoride | 0.05 |
| Pluronic F-127 ® (BASF, surfactant) | 1.40 |
| Na-phosphate buffer pH 7.0 | 1.10 |
| Sorbic acid | 0.20 |
| Sodium saccharin | 0.10 |
| Mixture MS2 and additional flavoring as in Example 3 | 0.25 |
| Color FD&C Blue #1 | 0.01 |
| Water | Ad 100.00 |

Example 5

Two wintergreen-flavored chewing gums having the mixture MSa (see example 1) according to the present invention are prepared according to the following formulation:

| Compound | Parts by weight Composition Cx | Parts by weight Composition Cy |
| --- | --- | --- |
| Sugar | 60.60 | 60.60 |
| Gum Base | 21.00 | 21.00 |
| Corn Syrup | 16.50 | 16.50 |
| Glycerin | 1.30 | 1.30 |
| Lecithin | 0.15 | 0.15 |
| Peppermint Oil | 0.40 | 0.40 |
| L-Menthol | 0.10 | 0.10 |
| N-ethyl-p-menthane-3-carboxamide | 0.05 | 0.05 |
| Methyl salicylate | 0.20 | — |
| Mixture MSa | 0.55 | 0.75 |

Chewing gum formulation Cx has a reduced methyl salicylate level.

In Chewing gum formulation Cy the methyl salicylate is entirely replaced by the mixture MSa.

The chewing gum formulations were prepared by melting the gum base at a temperature of about 85 to 90° C. and then adding with mixing the lecithin followed by adding the corn syrup and ⅓ of the sugar and again mixing until a homogenous mixture was obtained, approximately 5 minutes total time. The methyl salicylate and/or mixture MSa and glycerin were then added and mixed for about 2 minutes each followed by the remaining sugar which was mixed until a homogenous mixture was obtained, about 2 minutes. The formulation was cooled to about 40 to 45° C. and the menthol and carboxamide compound added and mixed into the formulation. The formulations were then cut into slab shapes.

These formulations were subjected to sensory evaluation studies. The chewing gum formulations Cx and Cy had the characteristic wintergreen taste and long-lasting cooling and breath freshening effects.

Example 6

A fragrance compositions (perfume oil) composition having the following formulation was produced, into which mixture MS1 was incorporated.

| Compound | Parts by weight |
| --- | --- |
| Red Berries extract | 50 |
| Bergamot oil bergapten-free | 80 |
| Cardamom absolute | 25 |
| Cyclopentadecanolide (1) | 150 |
| Cypress oil | 5 |
| Eugenol | 50 |
| Ginger oil synthetic | 60 |
| Methyl dihydrojasmonate | 100 |
| Iso E Super ® (2) | 150 |
| Amarocit ® (1) | 50 |
| Muscone | 50 |
| Clary sage oil | 75 |
| Vertocitral ® (1) | 45 |
| Vetiver oil | 10 |
| Mixture MS1 as in Example 2 | 110 |

Suppliers:
(1): Symrise GmbH & Co. KG, Germany, Holzminden
(2): International Flavors & Fragrances, USA, New Jersey, Union Beach

The invention claimed is:

1. Mixture comprising
   A) dihydroanethole,
   B) o-anisaldehyde
   C) 1,3-dimethoxybenzene,
   D) 2'-hydroxyacetophenone, and optionally
   E) 2-methoxyacetophenone, wherein
the amounts of compounds A), B), C), and D) and the ratio of compounds A):B):C):D) are adjusted so that the mixture provides a wintergreen flavor or odor.

2. Mixture according to claim 1, wherein the ratio of compounds A):B):C):D):E) in parts by weight is about 5-80:10-90:100-500: 100-500:0-200.

3. Fragrance or flavoring composition comprising an organoleptically effective amount of a mixture according to claim 1.

4. Fragrance or flavoring composition according to claim 3, wherein the composition possesses a wintergreen flavor or odor (i) resulting from or (ii) enhanced by the amount of the mixture present.

5. Fragrance or flavoring composition according to claim 4, the composition further comprising methyl salicylate, and wherein the ratio in parts by weight of methyl salicylate: said mixture of A), B), C), and D) is in the range of from 10:1 to 1:20.

6. Perfumed or flavored product comprising a mixture according to claim 1.

7. Product according to claim 6, characterized in that the product possesses a wintergreen flavor or odor (i) resulting from or (ii) enhanced by an amount of said mixture.

8. Product according to claim 6, wherein the product is a chewing gum, a toothpaste or a mouthwash.

9. Product according to claim 6, wherein the product has a pH from about 7.5 to about 12.

10. Perfumed product according to claim 6, wherein said product contains about 0.05 to 5% by weight of said mixture.

11. Flavored product according to claim 6, wherein said product contains about 0.05 to 2% by weight of said mixture.

12. Product according to claim 6, characterized in that the product comprises less than 0.1% by weight of methyl salicylate.

13. Method of adding a wintergreen odor, flavor or note to a product or enhancing the wintergreen odor, flavor or note of a product, the method comprising the step of adding to the product or incorporating into the product an effective amount of a mixture according to claim 1.

14. Method according to claim 13, wherein the product after addition of said mixture comprises less than 0.1% by weight of methyl salicylate.

15. Method according to claim 13, wherein the product is a chewing gum, a toothpaste or a mouthwash.

16. Method of reducing the level of methyl salicylate in a wintergreen fragrance or flavoring composition, the method comprising the step of substituting a portion or all of the methyl salicylate in the composition by a mixture according to claim 1.

17. A mixture according to claim 1, having a wintergreen flavor or odor consisting essentially of dihydroanethole, o-anisaldehyde, 1,3-dimethoxybenzene and 2'-hydroxyacetophenone.

18. The fragrance or flavoring composition of claim 3, wherein said mixture comprises dihydroanethole, o-anisaldehyde, 1,3-dimethoxybenzene, 2'-hydroxyacetophenone, and 2-methoxyacetophenone.

19. The fragrance or flavoring composition of claim 5, wherein the ratio of methyl salicylate to said mixture is from 4:1 to 1:10 parts by weight.

* * * * *